US00PP32271P2

(12) United States Plant Patent
Ferguson et al.

(10) Patent No.: US PP32,271 P2
(45) Date of Patent: Oct. 6, 2020

(54) STRAWBERRY PLANT VARIETY NAMED 'DRISSTRAWSEVENTYSEVEN'

(50) Latin Name: ***Fragaria* x *ananassa***
Varietal Denomination: DrisStrawSeventySeven

(71) Applicant: Driscoll's, Inc., Watsonville, CA (US)

(72) Inventors: Michael D. Ferguson, Watsonville, CA (US); Penny Nguyen, Watsonville, CA (US)

(73) Assignee: Driscoll's, Inc., Watsonville, CA (US)

( * ) Notice: Subject to any disclaimer, the term of this patent is extended or adjusted under 35 U.S.C. 154(b) by 0 days.

(21) Appl. No.: 16/501,759

(22) Filed: Jun. 4, 2019

(51) Int. Cl.
*A01H 5/08* (2018.01)
*A01H 6/74* (2018.01)

(52) U.S. Cl.
USPC ..... Plt./209

(58) Field of Classification Search
USPC ..... Plt./156, 208, 209
See application file for complete search history.

(56) References Cited

U.S. PATENT DOCUMENTS

PP1,745 P 8/1958 Lang
PP3,981 P 11/1976 Bringhurst et al.
PP4,487 P 11/1979 Bringhurst et al.
PP4,538 P 5/1980 Bringhurst et al.
PP5,262 P 7/1984 Voth et al.
PP5,265 P 7/1984 Voth et al.
PP5,266 P 7/1984 Bringhurst et al.
PP5,300 P 10/1984 Johnson Jr.
PP5,840 P 12/1986 Johnson, Jr. et al.
PP6,191 P 5/1988 Johnson, Jr. et al.
PP6,231 P 7/1988 Johnson, Jr. et al.
PP6,578 P 1/1989 Voth et al.
PP6,579 P 1/1989 Bringhurst et al.
PP7,024 P 9/1989 Johnson, Jr. et al.
PP7,172 P 2/1990 Voth et al.
PP7,522 P 5/1991 Johnson, Jr. et al.
PP7,614 P 8/1991 Bringhurst et al.
PP7,615 P 8/1991 Bringhurst et al.
PP8,086 P 1/1993 Nelson et al.
PP8,205 P 4/1993 Nelson et al.
PP8,649 P 3/1994 Sjulin et al.
PP8,661 P 3/1994 Bringhurst et al.
PP8,708 P 5/1994 Voth et al.
PP8,745 P 5/1994 Sjulin et al.
PP9,130 P 5/1995 Sjulin et al.
PP9,909 P 6/1997 Ackerman et al.
PP10,221 P 2/1998 Sjulin et al.
PP10,534 P 8/1998 Sjulin et al.
PP10,642 P 10/1998 Amorao et al.
PP11,035 P 8/1999 Mowrey et al.
PP11,277 P 3/2000 Gilford et al.
PP11,279 P 3/2000 Gilford et al.
PP11,522 P 9/2000 Amorao et al.
PP11,548 P 10/2000 Amorao et al.
PP11,554 P 10/2000 Sjulin et al.
PP11,639 P 11/2000 Mowrey et al.
PP12,186 P2 11/2001 Gilford et al.
PP12,436 P2 3/2002 Amorao et al.
PP12,577 P2 4/2002 Amorao et al.
PP12,817 P2 7/2002 Gilford et al.
PP12,899 P2 9/2002 Mowrey et al.
PP13,386 P2 12/2002 Mowrey et al.
PP13,469 P3 1/2003 Larson et al.
PP14,005 P3 7/2003 Amorao et al.
PP14,062 P3 8/2003 Amorao et al.
PP14,109 P3 8/2003 Gilford et al.
PP14,771 P3 5/2004 Amorao et al.
PP15,145 P2 9/2004 Mowrey et al.
PP15,308 P2 11/2004 Sjulin et al.
PP15,375 P2 11/2004 Mowrey et al.
PP15,435 P2 12/2004 Sjulin et al.
PP15,596 P2 3/2005 Amorao et al.
PP15,731 P2 4/2005 Amorao et al.
PP15,752 P2 5/2005 Gilford et al.
PP16,070 P2 10/2005 Gilford et al.
PP16,238 P2 2/2006 Amorao et al.
PP16,241 P2 2/2006 Mowrey et al.
PP16,298 P2 2/2006 Gilford et al.
PP16,299 P2 2/2006 Gilford et al.
PP16,475 P2 4/2006 Gilford et al.
PP16,558 P3 5/2006 López
PP18,000 P2 9/2007 Meulenbroek
PP18,040 P3 9/2007 Mowrey et al.
PP18,041 P3 9/2007 Gilford
PP18,458 P2 1/2008 Ferguson et al.
PP18,575 P3 3/2008 Amorao et al.
PP18,878 P2 6/2008 Mowrey et al.
PP19,240 P2 9/2008 Gilford et al.
PP19,673 P3 2/2009 Ferguson et al.
PP19,767 P2 2/2009 Shaw et al.
PP20,248 P3 9/2009 Rogers et al.
PP20,363 P2 9/2009 Chandler
PP20,701 P2 2/2010 Gilford et al.
PP20,731 P2 2/2010 Mowrey et al.
PP20,733 P2 2/2010 Mowrey et al.
PP20,735 P2 2/2010 Ferguson
PP20,775 P2 2/2010 Mowrey et al.
PP20,922 P2 4/2010 Gilford et al.
PP21,538 P2 11/2010 Gilford et al.
PP21,559 P2 12/2010 Ferguson et al.
PP21,762 P2 3/2011 Stewart et al.
PP22,040 P3 7/2011 Stewart et al.
PP22,218 P2 11/2011 Ferguson
PP22,247 P2 11/2011 Ferguson
PP23,107 P2 10/2012 Ferguson et al.
PP23,148 P2 10/2012 Gilford et al.
PP23,377 P2 2/2013 Ferguson et al.

(Continued)

OTHER PUBLICATIONS

Fear et al., Unpublished U.S. Appl. No. 15/998,014, filed Jun. 11, 2018, titled "Strawberry Plant Variety Named 'DrisStrawFiftyEight'".

(Continued)

*Primary Examiner* — Susan McCormick Ewoldt
*Assistant Examiner* — Karen M Redden
(74) *Attorney, Agent, or Firm* — Morrison & Foerster LLP

(57) ABSTRACT

A new and distinct variety of strawberry plant named 'DrisStrawSeventySeven', selected for its fruit size, yield, flavor, plant architecture, and open canopy, is disclosed.

6 Drawing Sheets

(56) References Cited

U.S. PATENT DOCUMENTS

| | | | |
|---|---|---|---|
| PP23,378 | P2 | 2/2013 | Pullen et al. |
| PP23,382 | P2 | 2/2013 | Ferguson et al. |
| PP23,383 | P2 | 2/2013 | Ferguson et al. |
| PP23,400 | P2 | 2/2013 | Ferguson et al. |
| PP23,401 | P2 | 2/2013 | Pullen et al. |
| PP23,459 | P2 | 3/2013 | Stewart et al. |
| PP23,506 | P3 | 4/2013 | Ferguson et al. |
| PP23,517 | P3 | 4/2013 | Ferguson et al. |
| PP24,096 | P3 | 12/2013 | Fear et al. |
| PP24,317 | P3 | 3/2014 | Ferguson et al. |
| PP24,333 | P3 | 3/2014 | Vitten et al. |
| PP24,395 | P3 | 4/2014 | Vitten et al. |
| PP24,533 | P3 | 6/2014 | Ferguson et al. |
| PP24,745 | P2 | 8/2014 | Vitten et al. |
| PP25,408 | P3 | 4/2015 | Vitten et al. |
| PP25,437 | P3 | 4/2015 | Vitten et al. |
| PP25,698 | P3 | 7/2015 | Ferguson et al. |
| PP25,699 | P3 | 7/2015 | Stewart et al. |
| PP25,747 | P3 | 7/2015 | Kibbe et al. |
| PP25,866 | P3 | 9/2015 | Ferguson et al. |
| PP26,800 | P3 | 6/2016 | Stewart et al. |
| PP26,801 | P3 | 6/2016 | Stewart et al. |
| PP26,802 | P3 | 6/2016 | Rodriguez Alcazar et al. |
| PP27,442 | P2 | 12/2016 | Kibbe et al. |
| PP27,645 | P3 | 2/2017 | Vitten et al. |
| PP27,682 | P3 | 2/2017 | Kibbe et al. |
| PP27,711 | P3 | 2/2017 | Vitten et al. |
| PP27,813 | P3 | 3/2017 | Ferguson et al. |
| PP29,289 | P3 | 5/2018 | Vitten et al. |
| PP29,728 | P2 | 10/2018 | Stewart et al. |
| PP29,729 | P2 | 10/2018 | Kibbe et al. |
| PP29,730 | P2 | 10/2018 | Kibbe et al. |
| PP29,731 | P2 | 10/2018 | Ferguson et al. |
| PP29,747 | P2 | 10/2018 | Vitten et al. |
| PP29,748 | P2 | 10/2018 | Vitten et al. |
| PP29,749 | P2 | 10/2018 | Stewart et al. |
| 2003/0079263 | P1 | 4/2003 | Gilford et al. |
| 2013/0276182 | P1 | 10/2013 | Fear et al. |

OTHER PUBLICATIONS

Ferguson et al., Unpublished U.S. Appl. No. 15/998,317, filed Aug. 3, 2018, titled "Strawberry Plant Variety Named 'DrisStrawSixty'".

Ferguson et al., Unpublished U.S. Appl. No. 16/501,758, filed Jun. 4, 2019, titled "Strawberry Plant Variety Named 'DrisStrawSeventySix".

Ferguson et al., Unpublished U.S. Appl. No. 16/501,428, filed Apr. 12, 2019, titled "Strawberry Plant Variety Named 'DrisStrawSeventyFive'".

Jacobs et al., Unpublished U.S. Appl. No. 16/501,501, filed Apr. 18, 2019, titled "Strawberry Plant Variety Named 'DrisStrawSeventy'".

Mendoza et al., Unpublished U.S. Appl. No. 16/350,139, filed Oct. 2, 2018, titled "Strawberry Plant Variety Named 'DrisStrawSixtySeven'".

Mendoza et al., Unpublished U.S. Appl. No. 15/998,020, filed Jun. 12, 2018, titled "Strawberry Plant Variety Named 'DrisStrawSixtyOne'".

Mendoza et al., Unpublished U.S. Appl. No. 15/998,169, filed Jul. 12, 2018, titled "Strawberry Plant Variety Named 'DrisStrawSixtyThree'".

Mendoza et al., Unpublished U.S. Appl. No. 15/998,170, filed Jul. 12, 2018, titled "Strawberry Plant Variety Named 'DrisStrawSixtyTwo'".

Mendoza et al., Unpublished U.S. Appl. No. 16/501,602, filed May 7, 2019, titled "Strawberry Plant Variety Named 'DrisStrawSixtyEight'".

Pakozdi et al., Unpublished U.S. Appl. No. 16/501,198, filed Mar. 5, 2019, titled "Strawberry Plant Variety Named 'DrisStrawSeventyThree'".

Pakozdi et al., Unpublished U.S. Appl. No. 15/998,015, filed Jun. 11, 2018, titled "Strawberry Plant Variety Named 'DrisStrawFiftyNine'".

Pakozdi et al., Unpublished U.S. Appl. No. 15/998,028, filed Jun. 14, 2018, titled "Strawberry Plant Variety Named 'DrisStrawSixtyFive'".

Pakozdi et al., Unpublished U.S. Appl. No. 16/501,182, filed Mar. 5, 2019, titled "Strawberry Plant Variety Named 'DrisStrawSeventyFour'".

Pakozdi et al., Unpublished U.S. Appl. No. 16/501,200, filed Mar. 5, 2019, titled "Strawberry Plant Variety Named 'DrisStrawSeventyTwo'".

Stewart et al., Unpublished U.S. Appl. No. 16/350,432, filed Nov. 14, 2018, titled "Strawberry Plant Variety Named 'DrisStrawSixtySix'".

Stewart et al., Unpublished U.S. Appl. No. 15/998,031, filed Jun. 14, 2018, titled "Strawberry Plant Variety Named 'DrisStrawSixtyFour'".

Stewart et al., Unpublished U.S. Appl. No. 16/501,449, filed Apr. 17, 2019, titled "Strawberry Plant Variety Named 'DrisStrawSeventyOne'".

STRAWBERRY PLANT VARIETY NAMED 'DRISSTRAWSEVENTYSEVEN'

Latin name:

Botanical classification: *Fragaria* x *ananassa*.

Varietal denomination The varietal denomination of the claimed variety of strawberry plant is 'DrisStrawSeventySeven'.

BACKGROUND OF THE INVENTION

Cultivated strawberry is a hybrid species of the genus *Fragaria* that is grown worldwide for its fruit. Modern strawberry was first bred in Brittany, France, in the 18$^{th}$ century by crossing *Fragaria virginiana* with *Fragaria chiloensis*. Strawberry fruit is an aggregate accessory fruit, with the fleshy part of the fruit being derived from the receptacle that holds the ovaries.

Strawberry varieties vary widely in color, size, shape, flavor, season of ripening, degree of fertility, and susceptibility to disease. Certain varieties vary in foliage, and some vary in the relative development of their reproductive organs. Typically, strawberry flowers appear hermaphroditic in structure, but function as either male or female. Generally, commercial production of strawberry plants involves propagation from runners and distribution as either plugs or bare root plants. Cultivation is either perennial or annual plasticulture. During the off season, strawberries can also be produced in greenhouses.

Strawberry fruit is widely appreciated for its characteristic bright red color, aroma, juicy texture, and sweetness. Strawberry fruit is a popular fruit that is generally consumed either fresh or in prepared foods, such as preserves and baked goods.

Strawberry is an important and valuable fruit crop. Accordingly, there is a need for new varieties of strawberry plants. In particular, there is a need for improved varieties of strawberry plant that are stable, high yielding, and agronomically sound.

SUMMARY OF THE INVENTION

In order to meet these needs, the present invention is directed to an improved variety of strawberry plant. In particular, the invention relates to a new and distinct variety of strawberry plant (*Fragaria* x *ananassa*), which has been denominated as 'DrisStrawSeventySeven'.

Strawberry plant variety 'DrisStrawSeventySeven' originated from a cross between the proprietary female parent '92T351' (unpatented) and the proprietary male parent '69U144' (unpatented). Progeny plants from this cross, including 'DrisStrawSeventySeven', were asexually propagated via stolons in McArthur, Shasta County, Calif. in September of 2012. Strawberry plant variety 'DrisStrawSeventySeven' was later specifically identified and selected in Ventura County, Calif. in January of 2013.

'DrisStrawSeventySeven' was subsequently asexually propagated via stolons, and underwent further testing at a farm in Oxnard, Ventura County, Calif. for seven years (2012 to 2019). The present variety has been found to be stable and reproduce true to type through successive asexual propagations via stolons.

'DrisStrawSeventySeven' exhibits the following distinguishing characteristics when grown under normal horticultural practices in Oxnard, Ventura County, Calif.:

1. Inflorescence on the same level as foliage;
2. Cordate shape of fruit; and
3. Partially remontant type of bearing.

'DrisStrawSeventySeven' was selected for its fruit size, yield, flavor, plant architecture, and open canopy.

DESCRIPTION OF THE DRAWINGS

This new strawberry plant is illustrated by the accompanying photographs which show fruit of the plant, flowers, leaves, and the plants. The colors shown are as true as can be reasonably obtained by conventional photographic procedures. The photographs are of plants that are twenty-five weeks old.

DETAILED BOTANICAL DESCRIPTION

Figure 1:
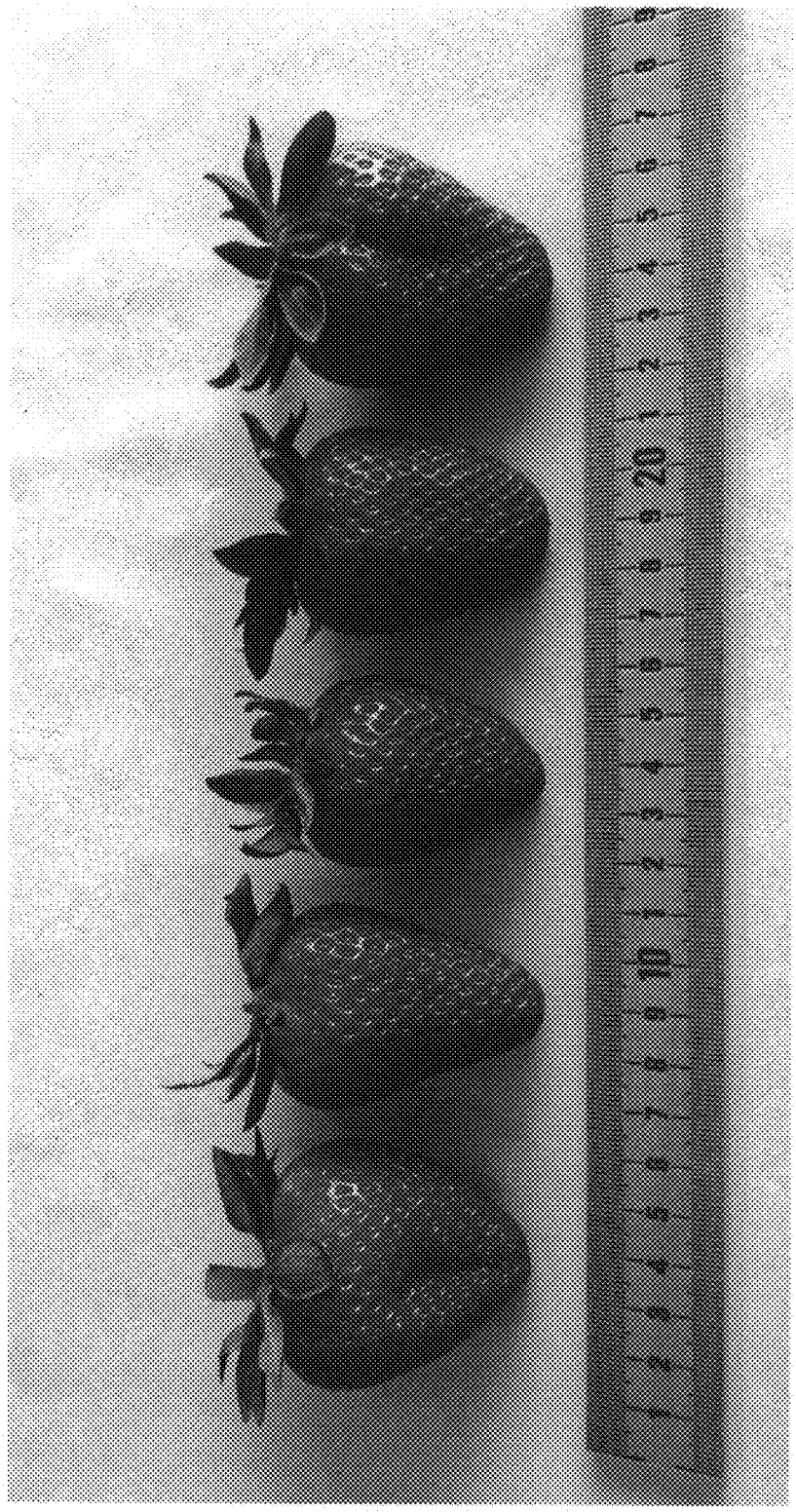
FIG. 1 illustrates whole fruit of variety 'DrisStrawSeventySeven'.
Figure 2:
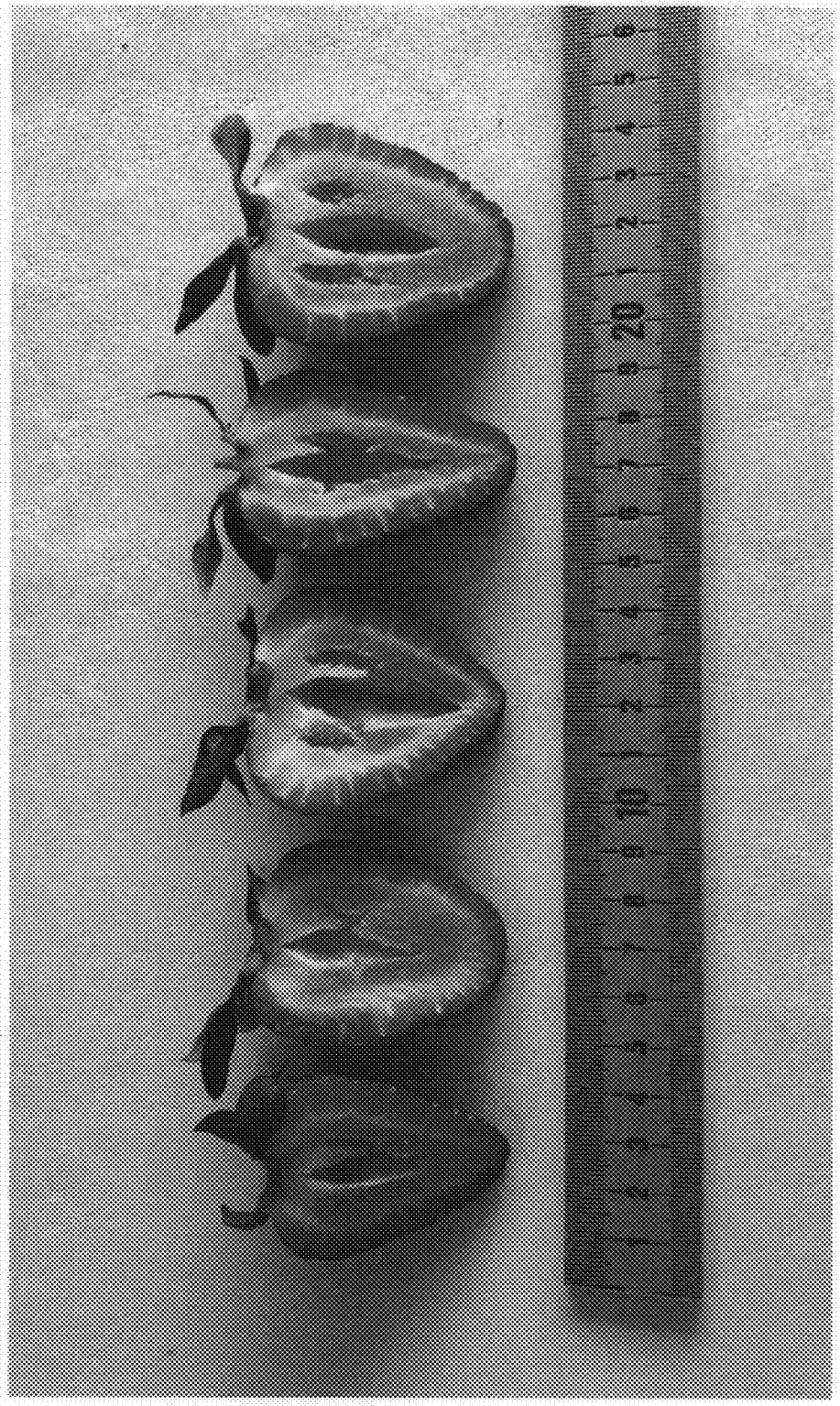
FIG. 2 illustrates longitudinal sections of fruit of variety 'DrisStrawSeventySeven'.
Figure 3:
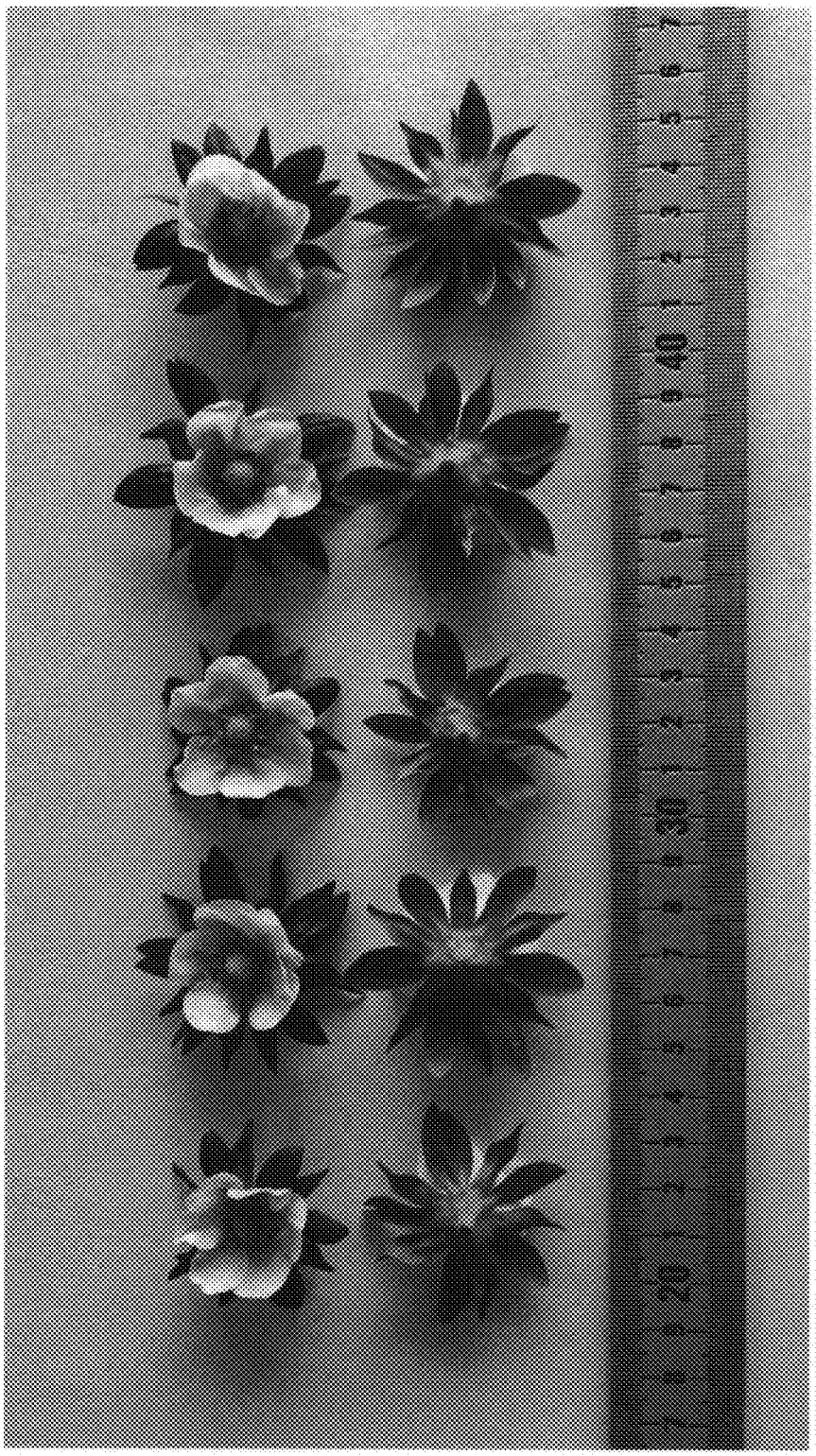
FIG. 3 shows the upper and lower surfaces of flowers of variety 'DrisStrawSeventySeven'.
Figures 4A, 4B:
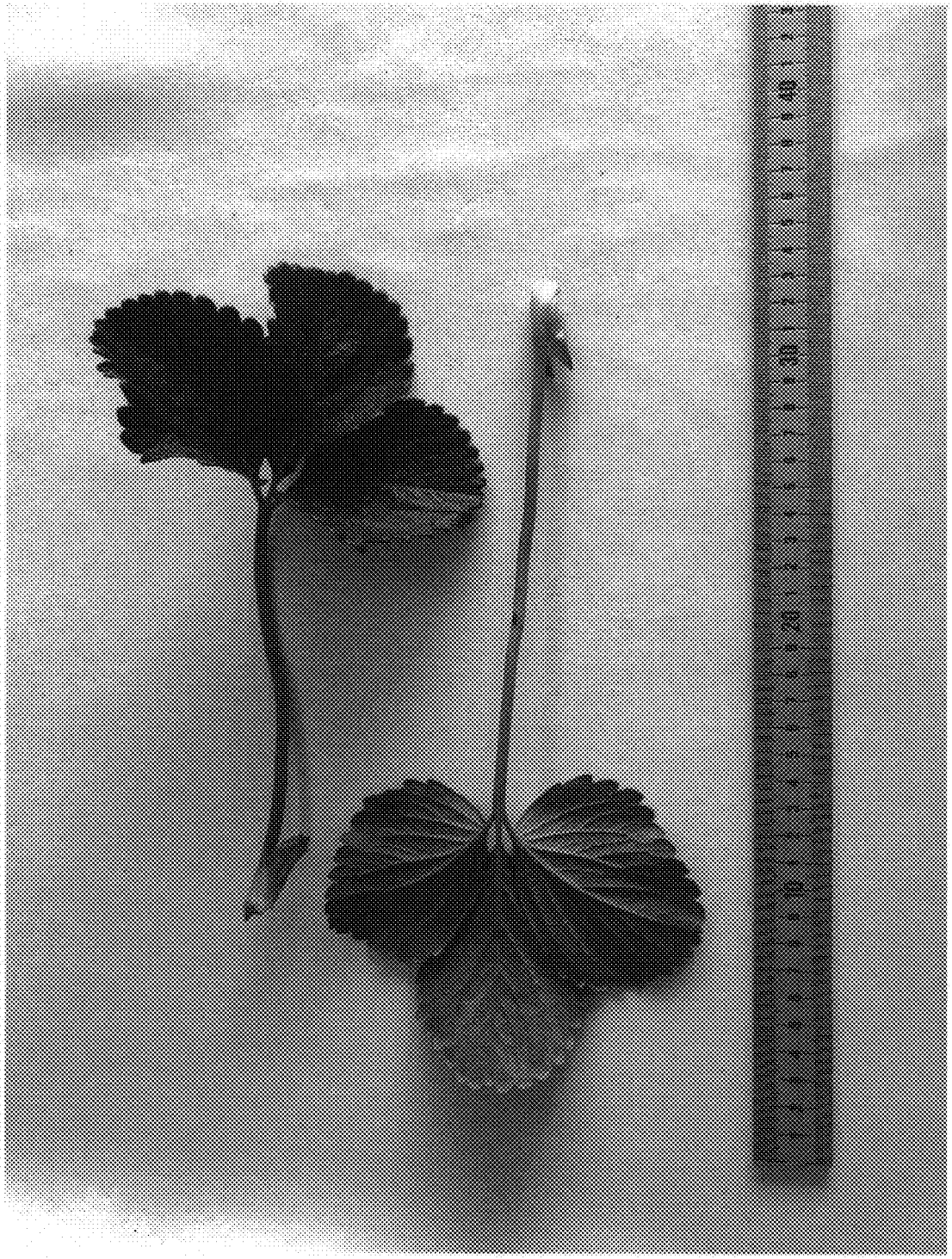
FIG. 4A shows the lower surface of a leaf of variety 'DrisStrawSeventySeven'.
FIG. 4B shows the upper surface of a leaf of variety 'DrisStrawSeventySeven'.
Figure 5:
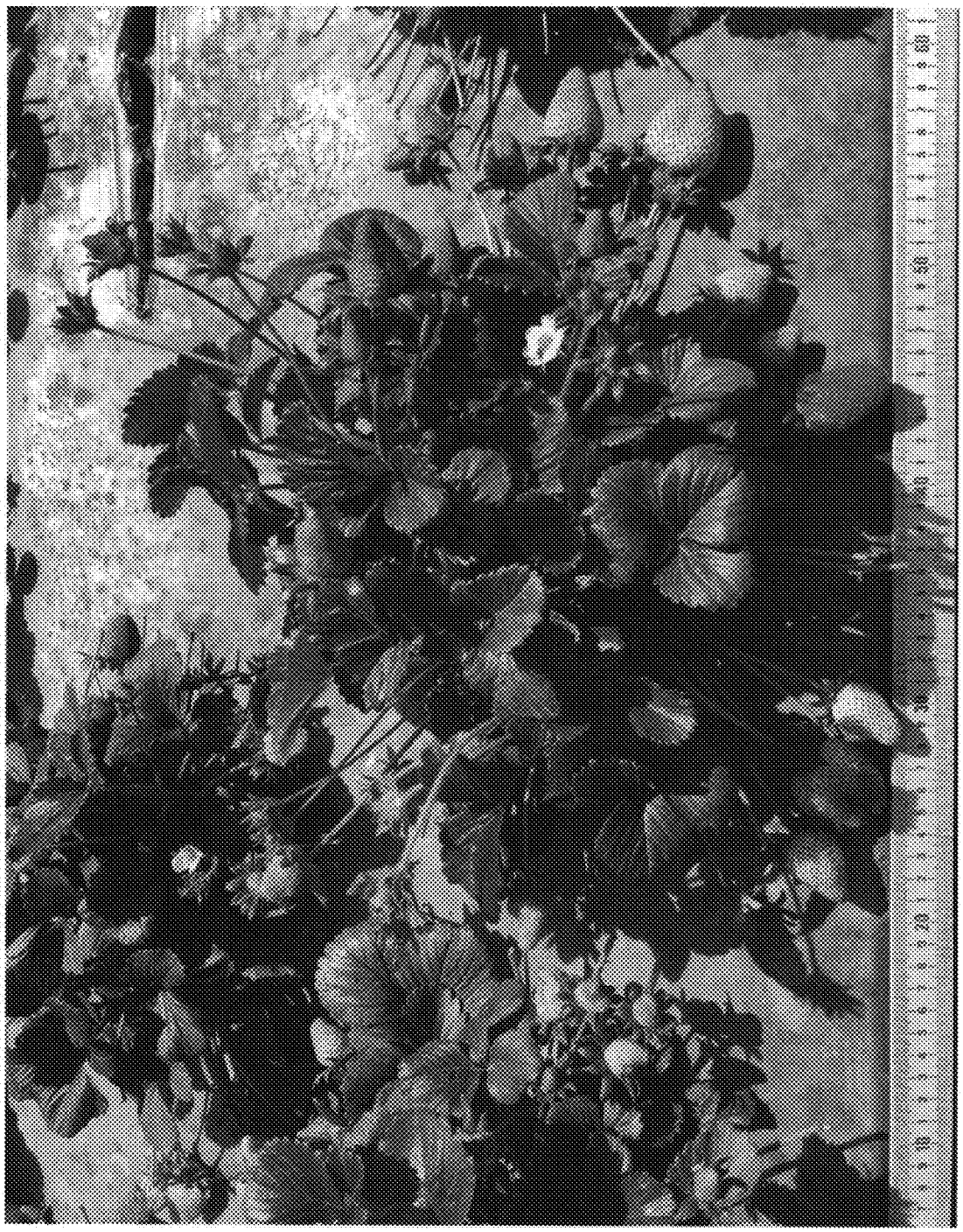
FIG. 5 illustrates a plant of variety 'DrisStrawSeventySeven'.
Figure 6:
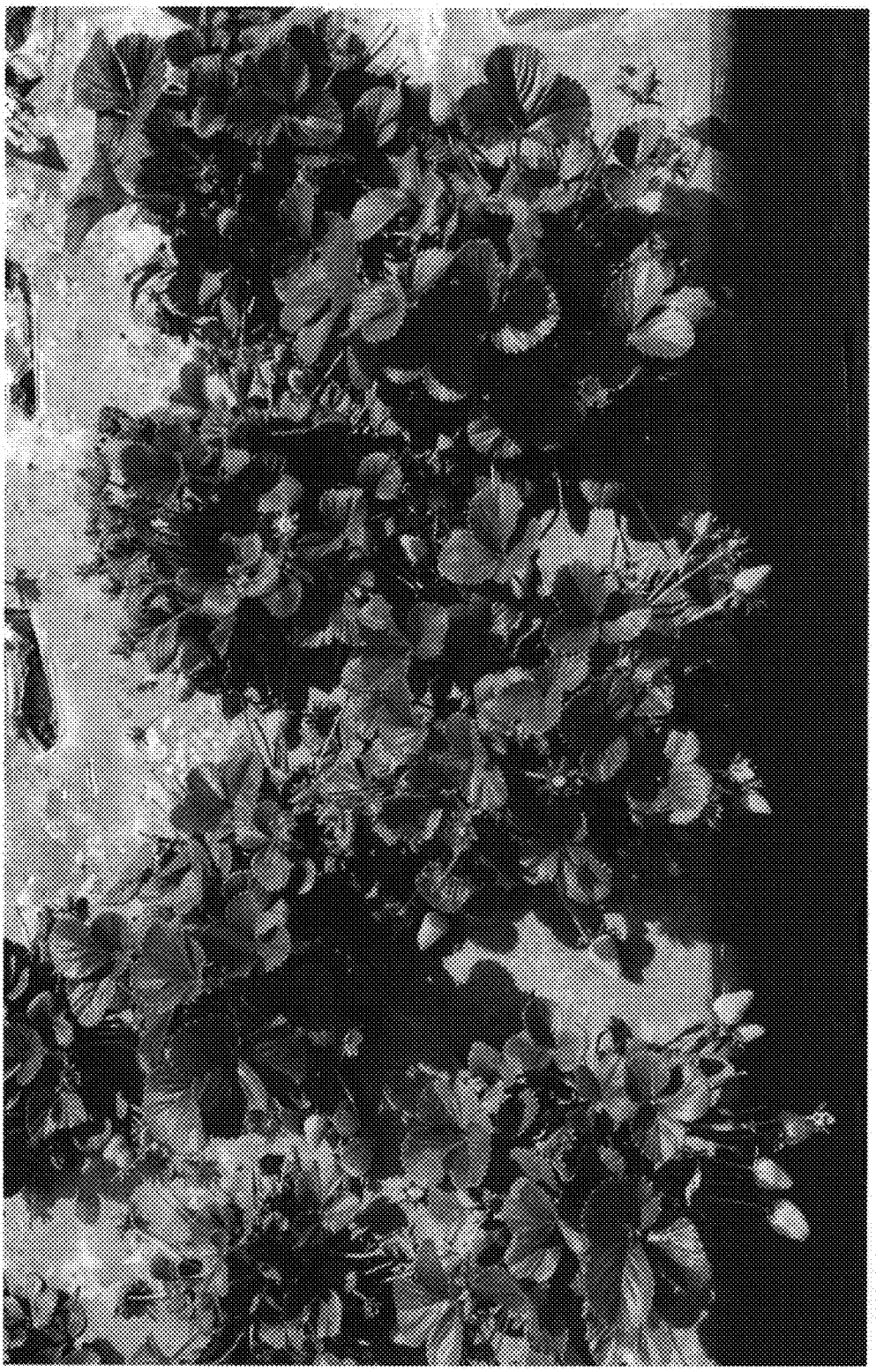
FIG. 6 illustrates a field of variety 'DrisStrawSeventySeven'.

The following detailed descriptions set forth the distinctive characteristics of 'DrisStrawSeventySeven'. The data which define these characteristics is based on observations taken in Ventura County, Calif. from 2012 to 2019. This description is in accordance with UPOV terminology. Color designations, color descriptions, and other phenotypical descriptions may deviate from the stated values and descriptions depending upon variation in environmental, seasonal, climatic, and cultural conditions. 'DrisStrawSeventySeven' has not been observed under all possible environmental conditions. The botanical description of 'DrisStrawSeventySeven' was taken from plants that were twenty-five weeks old. The indicated values represent averages calculated from measurements of several plants. Color references are primarily to The R.H.S. Colour Chart of The Royal Horticultural Society of London (R.H.S.) (2007 edition). Descriptive terminology follows the *Plant Identification Terminology, An Illustrated Glossary,* 2$^{nd}$ edition by James G. Harris and Melinda Woolf Harris, unless where otherwise defined.

Classification:

*Species.*—*Fragaria* x *ananassa*.

*Common name.*—Strawberry.

*Denomination.*—'DrisStrawSeventySeven'.

Parentage:

*Female parent.*—The proprietary variety '92T351' (unpatented).

*Male parent.*—The proprietary variety '69U144' (unpatented).

Plant:

*Height.*—26.54 cm.

*Diameter.*—38.35 cm.

*Number of crowns per plant.*—5.

*Growth habit.*—Semi-upright.

Stolon:

*Average number of daughter plants per square foot.*—10.

*Diameter at bract.*—4.21 mm.

*Anthocyanin coloration.*—Medium.

*Anthocyanin color.*—RHS N34B (Strong reddish orange).

*Overall color*.—RHS 143C (Strong yellow-green).
*Pubescence*.—Dense.

Leaf:

*Number of leaflets*.—Three only.
*Color of upper surface*.—RHS 137A (Moderate olive green).
*Color of lower surface*.—RHS 139C (Moderate yellow-green).
*Texture*.—Medium.
*Vein color*.—RHS 139C (Moderate yellow-green).
*Venation pattern*.—Pinnate and conspicuous.
*Variegation*.—Absent.
*Terminal leaflets*.—Length: 9.42 cm. Width: 7.57 cm. Length/width ratio: 1.24. Number of teeth/terminal leaflet: 20. Shape of base: Obtuse. Margin: Serrate to crenate. Shape in cross section: Concave.
*Petiole*.—Length: 22.48 cm. Diameter: 5.3 mm. Attitude of hairs: Slightly outwards. Bract frequency (number present on each petiole): 0. Color: RHS 143C (Strong yellow-green).
*Petiolule*.—Length: 9.6 mm. Diameter: 2.5 mm. Color: RHS 143C (Strong yellow-green).
*Stipule*.—Length: 3.44 cm. Width: 11.6 mm. Anthocyanin coloration: Medium. Anthocyanin color: RHS 59B (Deep purple-red). Overall color: RHS 139D (Moderate yellow-green). Pubescence: Light.

Inflorescence:

*Position in relation to foliage*.—Same level.
*Pedicel*.—Attitude of hairs: Slightly outwards. Length: 185 mm. Color: RHS 143C (Strong yellow-green).
*Peduncle*.—Color: RHS 143C (Strong yellow-green). Diameter: 5.52 mm.
*Flower bud*.—Length: 16.05 mm. Width: 8.63 mm. Shape: Cup. Color: RHS 145B (Light yellow-green).
*Flower*.—Flower diameter (petal tip to petal tip on non-flattened flower): 27.5 mm. Arrangement of petals: Overlapping. Stamen: Present. Typical and observed number of flowers per plant: 44.
*Petal*.—Length: 11.7 mm. Width: 11.7 mm. Length/width ratio: 1. Typical and observed petal number: 6. Color of upper side: RHS NN155C (White). Color of lower surface: RHS 155D (Yellowish white). Texture: Thin.
*Calyx*.—Diameter (sepal tip to sepal tip, measured on back of flower): 54.7 mm.
*Sepal*.—Length (sepal tip to point of attachment to receptacle): 22.9 mm. Width: 4.6 mm. Typical and observed sepal number: 12. Overall color: RHS 137B (Moderate olive green). Texture: Medium.
*Stigma*.—Length: 0.36 mm. Width: 0.22 mm. Shape: Rounded. Color: RHS 135D (Light yellowish green).
*Style*.—Length: 1.62 mm. Width: 0.31 mm. Shape: Tubular. Color: RHS 136D (Light yellowish green).
*Ovary*.—Length: 11.98 mm. Width: 9.79 mm. Color: RHS 136D (Light yellowish green).
*Stamen*.—Length: 2.54 mm. Width: 0.68 mm. Color: RHS 135D (Light yellowish green).
*Anther*.—Length: 2.21 mm. Width: 1.34 mm. Shape: Lanceolate to elliptic. Color: RHS 13A (Vivid yellow).
*Pollen*.—Color: RHS 13A (Vivid yellow).

Fruit:

*Length*.—55.9 mm.
*Width*.—43.5 mm.
*Length/width ratio*.—1.3.
*Fruit hollow length*.—28.8 mm.
*Fruit hollow width*.—6.7 mm.
*Fruit hollow length/width ratio*.—4.3.
*Shape*.—Cordate.
*Color*.—RHS N45A (Moderate red).
*Position of achenes*.—Below surface.
*Number of achenes per fruit*.—367.
*Achene length*.—1.91 mm.
*Achene width*.—0.81 mm.
*Achene shape*.—Elliptical.
*Achene color*.—RHS N167A (Brownish orange).
*Position of calyx attachment*.—Level with fruit.
*Attitude of sepals*.—Upwards.
*Color of flesh* (*excluding core*).—RHS 34A (Vivid reddish orange).
*Color of core*.—RHS 34B (Vivid reddish orange).
*Fruit weight*.—33 grams.

Production:

*Flowering interval*.—October-May.
*Harvest interval*.—November-June.
*Type of bearing*.—Partially remontant.
*Productivity*.—6,109 kg to 8,343 kg of fruit per acre per season from five-month-old plants when grown in Oxnard, Ventura County, Calif.
*Market use of fruit*.—Fresh and processing markets.
*Shipping and storage characteristics*.—Following harvest, fruit can be stored for 9-11 days if maintained under cooled temperatures that are standard for strawberry storage.

Resistance to diseases, pests, and abiotic stress:

*Heat*.—Moderately resistant.
*Two-spotted spider mite* (*Tetranychus urticae*).—Moderately susceptible.
*Botrytis fruit rot* (*Botrytis cinerea*).—Moderately resistant.
*Powdery mildew* (*Podosphaera macularis*).—Moderately resistant.
*Anthracnose crown rot* (*Colletotrichum acutatum*).—Moderately resistant.
*Winter hardiness*.—Moderate.

COMPARISON WITH PARENTAL AND COMMERCIAL VARIETIES

'DrisStrawSeventySeven' differs from the proprietary female parent '92T351' (unpatented) in that 'DrisStrawSeventySeven' has earlier yields, produces fruit that are sweeter, firmer, and more aromatic, and has better rain tolerance as compared to '92T351'.

'DrisStrawSeventySeven' differs from the proprietary male parent '69U144' (unpatented) in that 'DrisStrawSeventySeven' has earlier yields, produces fruit that are sweeter, firmer, and more aromatic, and has better rain tolerance as compared to '69U144'.

'DrisStrawSeventySeven' differs from the commercial variety 'DrisStrawTwentySeven' (U.S. Plant Pat. No. 23,400) in that 'DrisStrawSeventySeven' has inflorescence on the same level as foliage, calyx attachment level with fruit, a cordate shape of fruit, and a partially remontant type of bearing, whereas 'DrisStrawTwentySeven' has inflorescence above foliage, calyx attachment raised from fruit, a conical shape of fruit, and a not remontant type of bearing.

'DrisStrawSeventySeven' differs from the commercial variety 'DrisStrawThirtySix' (U.S. Plant Pat. No. 25,698) in that 'DrisStrawSeventySeven' has inflorescence on same level as foliage, an obtuse shape of base of terminal leaflet, a cordate shape of fruit, and a partially remontant type of bearing, whereas 'DrisStrawThirtySix' has inflorescence above foliage, an acute shape of base of terminal leaflet, a conical shape of fruit, and a not remontant type of bearing.

We claim:

1. A new and distinct variety of strawberry plant named 'DrisStrawSeventySeven' as shown and described herein.

* * * * *